(12) United States Patent
Kalkman et al.

(10) Patent No.: US 8,109,128 B2
(45) Date of Patent: Feb. 7, 2012

(54) CAVITY-ENHANCED PHOTO ACOUSTIC TRACE GAS DETECTOR WITH IMPROVED FEEDBACK LOOP

(75) Inventors: Jeroen Kalkman, Eindhoven (NL); Maarten Marinus Johannes Wilhelm Van Herpen, Eindhoven (NL); Hans Willem Van Kesteren, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 422 days.

(21) Appl. No.: 12/438,574

(22) PCT Filed: Aug. 30, 2007

(86) PCT No.: PCT/IB2007/053495
§ 371 (c)(1),
(2), (4) Date: Feb. 24, 2009

(87) PCT Pub. No.: WO2008/026183
PCT Pub. Date: Mar. 6, 2008

(65) Prior Publication Data
US 2010/0011836 A1 Jan. 21, 2010

(30) Foreign Application Priority Data
Aug. 31, 2006 (EP) .................................. 06119851

(51) Int. Cl.
*G01N 21/17* (2006.01)
(52) U.S. Cl. ..................... 73/24.02; 73/24.06
(58) Field of Classification Search ............... 73/24.02, 73/24.06
See application file for complete search history.

(56) References Cited

U.S. PATENT DOCUMENTS
3,793,523 A * 2/1974 Desvignes et al. ......... 250/206.1
(Continued)

FOREIGN PATENT DOCUMENTS
JP 57-78239 A 5/1982

OTHER PUBLICATIONS
Davidsson, J. et al., "Experimental Improvements in Recording Gas-Phase Photoacoustic Spectra", The Journal of Physical Chemistry, vol. 94, No. 10, 1990, pp. 4069-4073.*
(Continued)

*Primary Examiner* — Daniel Larkin

(57) ABSTRACT

A photo acoustic trace gas detector (100) is provided for detecting a concentration of a trace gas in a gas mixture. The detector (100) comprises a light source (101) for producing a light beam and a light modulator (103) for modulating the light beam into a series of light pulses at a chopping frequency for generating sound waves in the gas mixture. The amplitude of the sound waves is a measure of the concentration of the trace gas. The detector (100) further comprises an optical cavity (104a, 104b) with the gas mixture. The optical cavity (104a, 104b) amplifies the light intensity of the light pulses. A transducer (109) converts the sound waves into electrical signals. A feed back loop (110, 111, 113, 114) regulates a ratio of a length of the optical cavity (104a, 104b) and a wavelength of the light beam for amplifying the light intensity of the light pulses in the optical cavity (104a, 104b). The feedback loop (110, 111, 113, 114) comprises ratio modulating means (113, 114) for modulating the ratio at a modulation frequency, a photo detector (110) for measuring the light intensity of the light pulses and adjusting means (111), coupled to the photo detector (100) and to the ratio modulating means (113, 114) for, in dependence of the measured light intensity, adjusting an average of the ratio. The chopping frequency is higher than the modulation frequency.

6 Claims, 5 Drawing Sheets

U.S. PATENT DOCUMENTS

| | | | | |
|---|---|---|---|---|
| 3,893,771 | A  * | 7/1975 | Bell | 356/402 |
| 4,817,413 | A  * | 4/1989 | Asano et al. | 73/24.02 |
| 7,101,340 | B1 * | 9/2006 | Braun | 600/532 |
| 7,106,763 | B2 * | 9/2006 | Tan et al. | 372/9 |
| 7,263,871 | B2 * | 9/2007 | Selker et al. | 73/24.02 |
| 7,277,177 | B2 * | 10/2007 | Augustine et al. | 356/437 |
| 7,921,693 | B2 * | 4/2011 | Van Herpen | 73/24.02 |
| 2004/0095579 | A1 * | 5/2004 | Bisson et al. | 356/432 |
| 2005/0117155 | A1 | 6/2005 | Kosterev | |

OTHER PUBLICATIONS

Fink, T. et al., "An Improved CO2 Laser Intracavity Photoacoustic Spectrometer for Trace Gas Analysis", Rev. Sci. Instrum., vol. 67, No. 11, Nov. 1996, pp. 4000-4004.*

Rossi Alessandro et al: "Optical enhancement of diode laser-photoacoustic trace gas detection by means of external Fabry-Perot cavity" Applied Physics Letters, vol. 87, No. 4, Jul. 22, 2005, pp. 41110-1-41110-3.

* cited by examiner

CAVITY-ENHANCED PHOTO ACOUSTIC TRACE GAS DETECTOR WITH IMPROVED FEEDBACK LOOP

TECHNICAL FIELD OF THE INVENTION

The invention relates to a photo acoustic trace gas detector for detecting a concentration of a trace gas in a gas mixture, the photo acoustic trace gas detector comprising a light source for producing a light beam, a light modulator for modulating the light beam into a series of light pulses at a chopping frequency for generating sound waves in the gas mixture, an amplitude of the sound waves being a measure of the concentration an optical cavity for containing the gas mixture and for amplification of a light intensity of the light pulses, a transducer for converting the sound waves into electrical signals, and a feedback loop for regulating a ratio of a length of the optical cavity and a wavelength of the light beam for the amplification of the light intensity of the light pulses in the optical cavity, the feedback loop comprising ratio modulating means for modulating the ratio at a modulation frequency, a photo detector for measuring the light intensity of the light pulses, and adjusting means, coupled to the photo detector and to the ratio modulating means for, in dependence of the measured light intensity, adjusting an average of the ratio.

BACKGROUND OF THE INVENTION

Such a detector is known from the article "Optical enhancement of diode laser-photo acoustic trace gas detection by means of external Fabry-Perot cavity" by Rossi et al., published in Applied Physics Letters, vol. 87, 2005. The detector described therein sends a chopped laser beam through a gas contained in an acoustic cell. The laser wavelength is tuned to excite particular molecules of the gas into a higher energy level. This excitation leads to an increase of the thermal energy, resulting in a local rise of the temperature and the pressure inside the acoustic cell. If the chopping frequency matches a resonance frequency of the acoustic cell, the pressure variations result in a standing acoustic wave. The acoustic waves are detected by a microphone in the acoustic cell. The resonance frequency of such an acoustic cell is typically between 500 Hz and a few kHz. In the detector of Rossi et al., a chopping frequency of 2.6 kHz is used for matching the resonance frequency of the acoustic cell.

Rossi et al. also describe using a Fabry-Perot cavity for amplifying the light intensity in the acoustic cell. The amplification is very advantageous because the sensitivity of the detector is proportional to the laser power. A feedback signal is obtained from a photodiode placed behind the Fabry-Perot cavity. In order to produce this feedback signal, the laser wavelength is weakly modulated by adding a small sinusoidal waveform to the power supply current. When the feedback signal exceeds a fixed threshold, the wavelength of the laser beam or the length of the cavity is adapted to bring the transmission back to the desired level. The photodiode does not provide a feedback signal when the chopper obstructs the passage of the light beam. As a result, the system can run out of its lock-loop for sudden disturbances, because it cannot respond sufficiently fast. In order to prevent this, a low response time is necessary such that the effect of harmonically turning the feedback signal on and off will be averaged out.

An important application of photo acoustic trace gas detectors is breath testing. Breath testing is a promising area of medical technology. Breath tests are non-invasive, user friendly and low cost. Prime examples of breath testing are monitoring of asthma, alcohol breath testing and detection of stomach disorders and acute organ rejection. First clinical trials show possible applications in the pre-screening of breast and lung cancer. These volatile biomarkers have typical concentrations in the parts per billion (ppb) range. Nitric oxide (NO) is one of the most important trace gases in the human breath, and elevated concentrations of NO can be found in asthmatic patients. Currently, exhaled NO levels at ppb concentrations can be only measured using expensive and bulky equipment based on chemiluminescence or far infrared optical absorption spectroscopy. A compact, hand-held, and low-cost NO sensor forms an interesting device that can be used to diagnose and monitor airway inflammation and can be used at the doctor's office and for medication control at home.

It is the challenge for these hand-held gas-analyzing devices to combine sufficient high sensitivity (ppb level) with a high robustness. Current photo acoustic trace gas detectors have the disadvantage that small form factor lasers (i.e. diode lasers) do not have sufficient laser power to reach the sensitivity required for trace gas detection. The use of an optical power enhancement cavity as described by Rossi et al. could increase the optical power, but that would lead to a slow feedback. When an optical enhancement cavity is used in combination with photo acoustics, the feedback signal is turned on and off intermittently by the chopper. Consequently, the cavity locking mechanism becomes very slow, which results in a system that is not robust enough for portable applications.

SUMMARY OF THE INVENTION

It is an object of the invention to provide a photo acoustic gas trace detector according to the opening paragraph with a fast feedback loop.

According to a first aspect of the invention, this object is achieved by providing a photo acoustic trace gas detector according to the opening paragraph, wherein the chopping frequency is higher than the modulation frequency.

When choosing the chopping frequency higher than the modulation frequency, the light is turned on and off multiple times during one period of the modulation of the wavelength or cavity length. The effect of the obstruction of the light beam will then be averaged over one period of the wavelength modulation and there are no long periods where the feedback signal is absent. The response time of the feedback loop can be much faster than in the previously known photo acoustic trace gas detectors with optical cavity.

Preferably, the chopping frequency is at least three times higher than the modulation frequency, for achieving the most advantageous effect.

In a preferred embodiment the transducer is a crystal oscillator. A crystal oscillator is much more sensitive than the microphone used in the above mentioned prior art system. Consequently, a more sensitive photo acoustic trace gas detector is obtained. As an additional advantage, the high sensitivity of the crystal oscillator makes the use of an acoustic cell unnecessary and thereby simplifies the construction of the detector. Furthermore, crystal oscillators generally resonate at higher frequencies than microphones and thereby enable applying a higher chopping frequency and a faster feedback loop. The higher robustness obtained thereby allows for using the trace gas detector in portable applications.

In a further embodiment the crystal oscillator is a quartz tuning fork. Quartz tuning forks have a high sensitivity and operate at a high frequency. Furthermore, quartz tuning forks are not very expensive because they are used on large scale, for example, for the manufacturing of digital watches.

These and other aspects of the invention are apparent from and will be elucidated with reference to the embodiments described hereinafter.

DETAILED DESCRIPTION OF THE INVENTION

Figure 1:
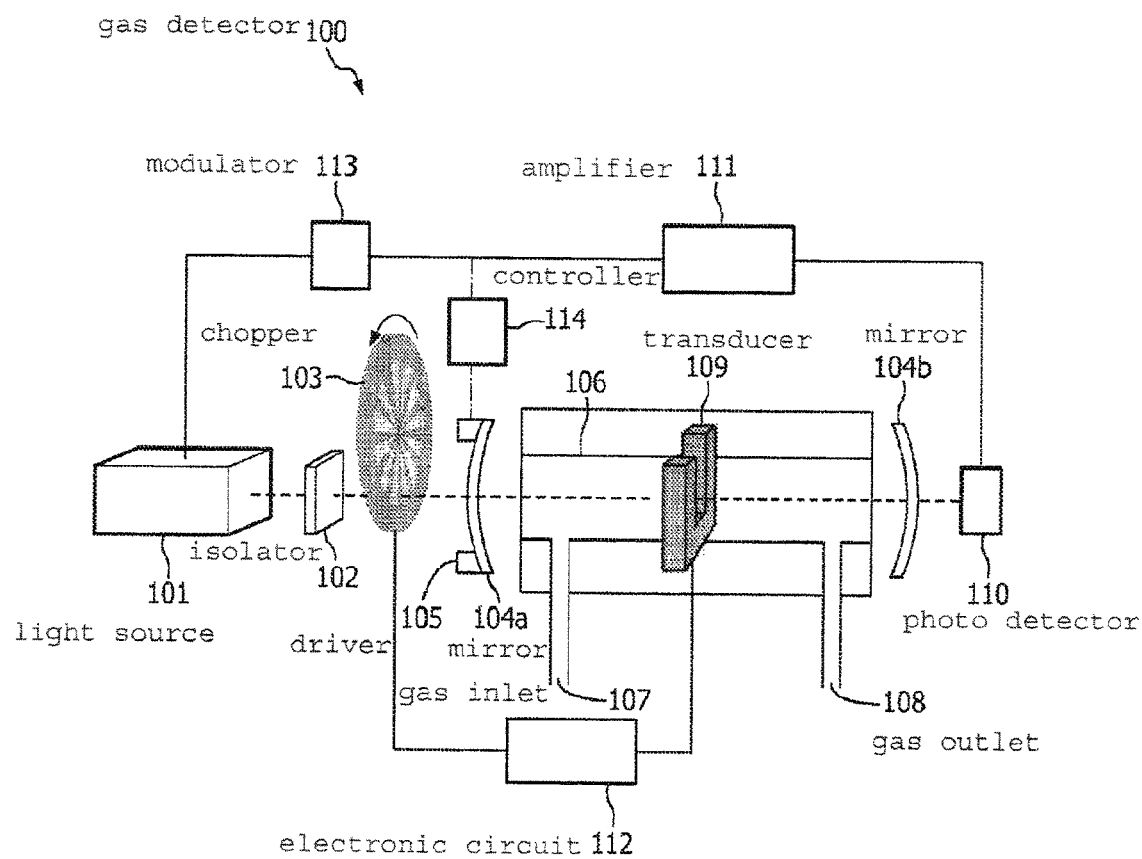
FIG. 1 schematically shows an embodiment of the photo acoustic trace gas detector according to the invention.

FIG. 1 shows a typical photo acoustic trace gas detector 100 according to the invention. A light source 101 provides a continuous wave laser beam and is modulated into a series of light pulses at a certain 'chopping' frequency by, e.g., a chopper 103, shutter or acousto-optic modulator. At higher chopping frequencies (>6 kHz), acousto-optic modulators are preferably used instead of a mechanical chopper. Alternatively, the light source 101 itself may provide the light pulses at a fixed chopping frequency. The light pulses are sent into an optical cavity, which is defined by two semi-transparent mirrors 104a and 104b. An optical isolator 102 is optionally placed between the light source 101 and the input mirror 104a to reduce the back reflectance of light from the cavity mirror 104a into the light source 101. The light pulses enter the optical cavity through input mirror 104a and are reflected many times between the two cavity mirrors 104a and 104b. If the distance between the two mirrors 104a and 104b and the wavelength of the laser are in resonance, standing waves occur and the light intensity is amplified. The light that is transmitted by the output mirror 104b is measured with a photo detector 110. The signal from the photo detector 110 is used as a feedback signal for the laser wavelength or the length of the optical cavity.

In an exemplary locked cavity scheme the laser wavelength and the cavity length are kept in resonance. In most designs either the laser wavelength or cavity length is modulated and the transmission or reflection of the laser through the cavity is monitored with a photo detector 110. The wavelength modulation is controlled by a wavelength modulator 113. The cavity length is modulated by a cavity length controller 114 that controls a piezo driver 105 which is attached to one of the cavity mirrors 104a, 104b. The change in transmission caused by the laser wavelength or cavity length modulation is then used as a feedback signal that is used to either drive an actuator, e.g. the piezo driver 105, attached to one of the cavity mirrors 104a, 104b (cavity length modulation) or to set the laser frequency (laser wavelength modulation).

The wavelength of the laser is typically scanned on the flank of a cavity resonance if it is locked to the cavity. When the laser wavelength gets out of resonance with the cavity (not including the small wavelength modulation of the laser) the transmitted intensity changes. A signal is then sent to the laser diode 101 to correct the wavelength and bring the transmission back to the desired level. Note that at maximum cavity transmission the wavelength modulation of the laser does not result in a change in transmission. Therefore the cavity should be operated just below maximum transmission. When the laser intensity changes (due to laser instability) the height of the resonance peak changes with a consequent change of the feedback amplitude as a result. The locking mechanism will move the laser to another frequency on the new resonance curve such that the same feedback amplitude is generated.

Inside the optical cavity a gas cell 106 is situated for containing the gas sample to be examined. Alternatively, the optical cavity is enclosed by the gas cell 106. Optionally, the gas cell 106 comprises a gas inlet 107 and a gas outlet 108 for allowing a gas flow through the gas cell 106. If the laser wavelength is tuned to a molecular transition, i.e. EI→EK, some of the gas molecules in the lower level EI will be excited into the upper level EK. By collisions with other atoms or molecules these excited molecules may transfer their excitation energy into translational, rotational, or vibrational energy of the collision partners. At thermal equilibrium this causes an increase of the thermal energy, resulting in a local rise of the temperature and pressure inside the gas cell 106. Every pulse of light will cause an increase in pressure after which the pressure can reduce again, before the next pulse arrives. This increase and decrease of pressure will result in an acoustic wave at the chopping frequency. The acoustic signals may be amplified using an acoustic cell with the right dimensions for resonating at the chopping frequency. Centered in the middle of the gas cell 106 is a transducer 109 for turning the acoustic waves into electrical signals which are provided to an electronic circuit 112 connected to the chopper 103. Preferably, the transducer 109 is a crystal oscillator, e.g. a quartz tuning fork, with a resonance frequency that can pick up the acoustic wave generated by the absorbed light in the gas. The use of a crystal oscillator may make the acoustic cell unnecessary.

Figure 2:
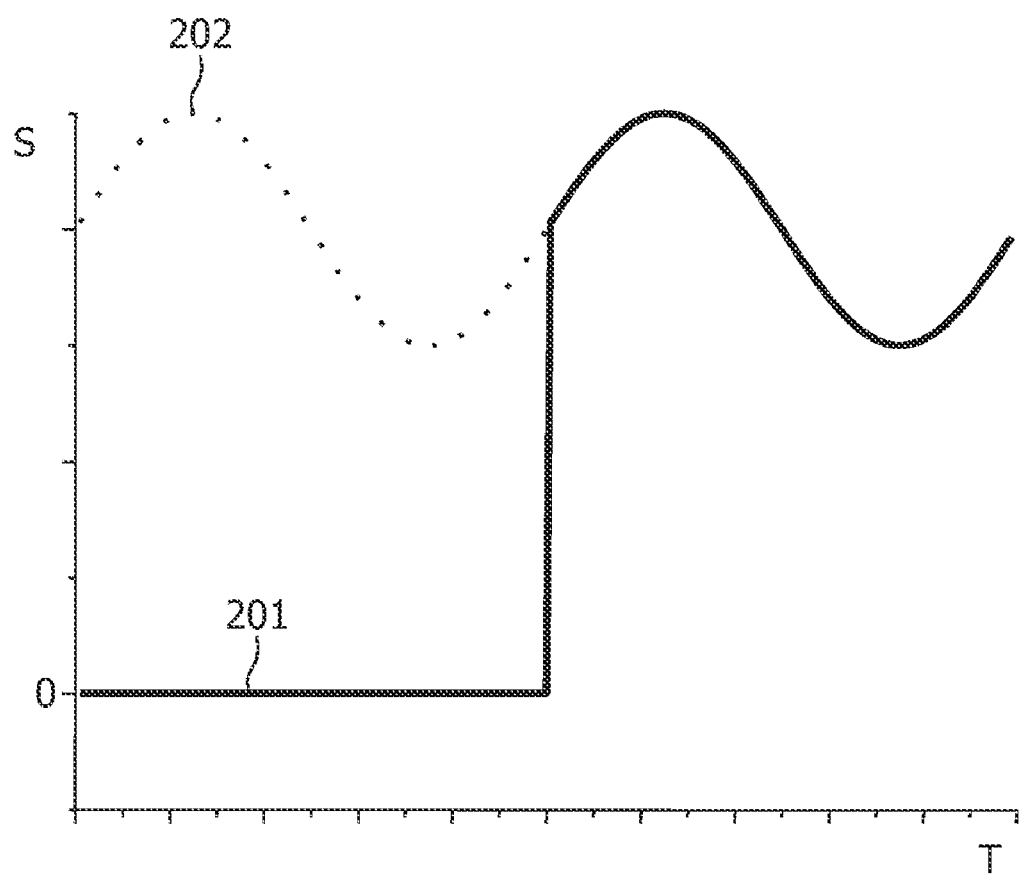
FIG. 2 shows a time dependence of signals in the feedback loop according to the prior art.
Figure 3:
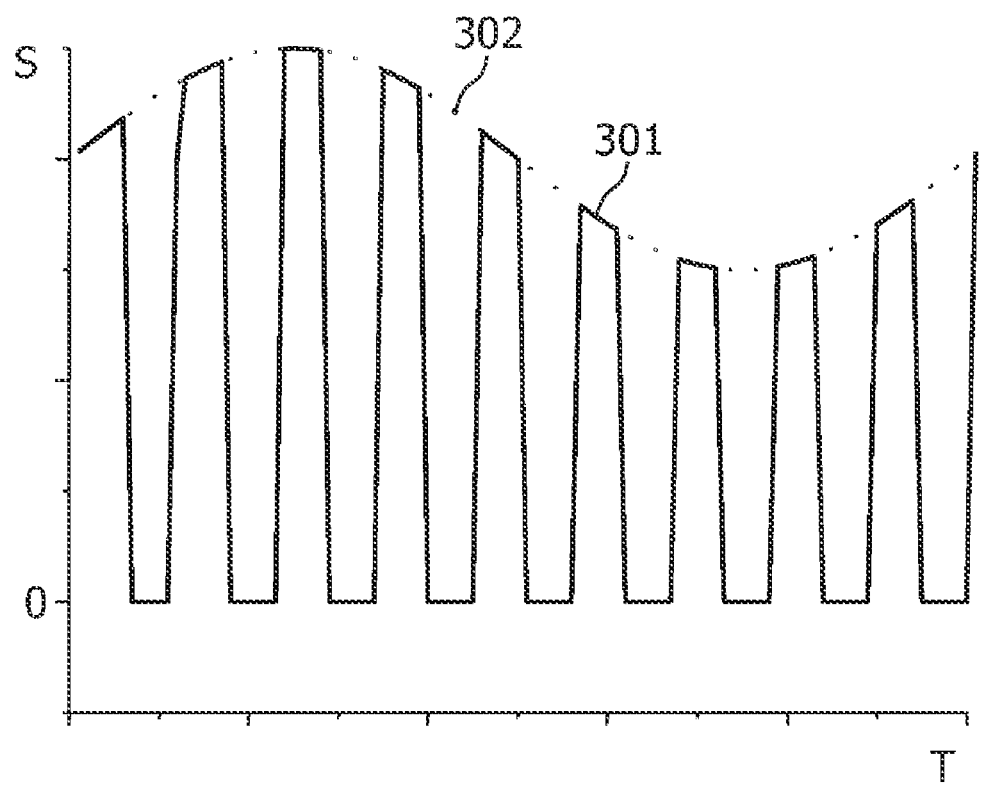
FIG. 3 shows a time dependence of signals in the feedback loop according to an embodiment of the present invention.

As will be elucidated with reference to FIGS. 2 and 3, the use of a chopping frequency above the modulation frequency makes it possible to reduce the response time of the feedback loop.

As will be elucidated with reference to FIGS. 2 and 3, the use of a chopping frequency above the modulation frequency makes it possible to reduce the response time of the feedback loop.

FIG. 2 shows a time dependence of signals in the feedback loop according to the prior art. A dotted line shows the driving signal 202 for the light source 101. Preferably, the light source 101 is a diode laser 101 and the driving signal 202 is provided by a laser driver. The driving signal 202 is also used as a reference signal for the feedback loop. The diode laser 101 provides a laser beam with a wavelength modulation corresponding to the driving signal 202. The laser beam is chopped by the chopper 103 and sent through the optical cavity. The amplification of the light intensity by the optical cavity is dependent on the wavelength of the laser beam. As a result, a modulated signal can be measured with detector 110. The detector signal 201 is sent to an electronic system 111, for example a lock-in amplifier, where the detector signal 201 is demodulated using the reference signal 202 of the modulation. The demodulated signal is indicative of the position of the laser wavelength with regard to the optimum wavelength for the optical cavity. If the signal is positive, the position is on one side of the resonance wavelength and if the signal is negative, the position is on the other side. The magnitude of the signal corresponds with the distance to the optimum position.

It is also possible to modulate the position of the cavity mirrors 104a, 104b instead of modulating the laser wavelength. The difference with the previous embodiments is that the modulation signal is now sent to the piezo driver 105 instead of the laser. The advantage of this embodiment is that since piezos are faster (>1 kHz) and more stable than the tuning of the laser wavelength the feedback can be faster and no laser stabilization has to be incorporated. Additionally, a laser may not be able to tune its wavelength at all, or the laser may not be able to tune its wavelength fast enough.

Depending on whether cavity length modulation or wavelength modulation is applied, the demodulated signal is sent to the piezo driver 105 or the laser driver (typically via an extra amplifier) via the respective ratio modulating means 114 or 113. Then the demodulated signal is added onto the voltage that is already being sent to the piezo driver 105 or laser driver. In this way, the cavity length or laser wavelength will become locked to the laser wavelength or cavity length, respectively.

Due to the chopping of the laser beam, half of the time, the detector signal 201 will be zero and is not usable for feedback. In the prior art (see Rossi et al.) this problem is solved by using a modulation frequency that is at least twice and preferably three times the chopping frequency. As can be seen in FIG. 2, this results in the detector signal 201 comprising at least one period of the modulation signal for every period of the chopping frequency. By monitoring the feedback signal 201 over a longer period, the chopping effect is averaged out. It is a disadvantage of this prior art method, that the averaging out of the chopping effect takes much time and results in a response time, too long for portable applications.

FIG. 3 shows a time dependence of signals in the feedback loop according to an embodiment of the present invention. According to the invention, the chopping frequency is higher than the modulation frequency of the laser wavelength or cavity mirror position. Preferably, a crystal oscillator is used that resonates at the chopping frequency. Due to the high sensitivity of the crystal oscillator 109, no acoustic cell is needed for amplification of the pressure variations. In this exemplary embodiment the chopping frequency is about a nine times the modulation frequency. Because there are no long periods 302 where the feedback signal 301 is absent, it is not necessary to monitor the feedback signal 301 over a long period for averaging out the chopping effect. Consequently the response time of the feedback loop is much shorter than in the prior art.

Figure 4:
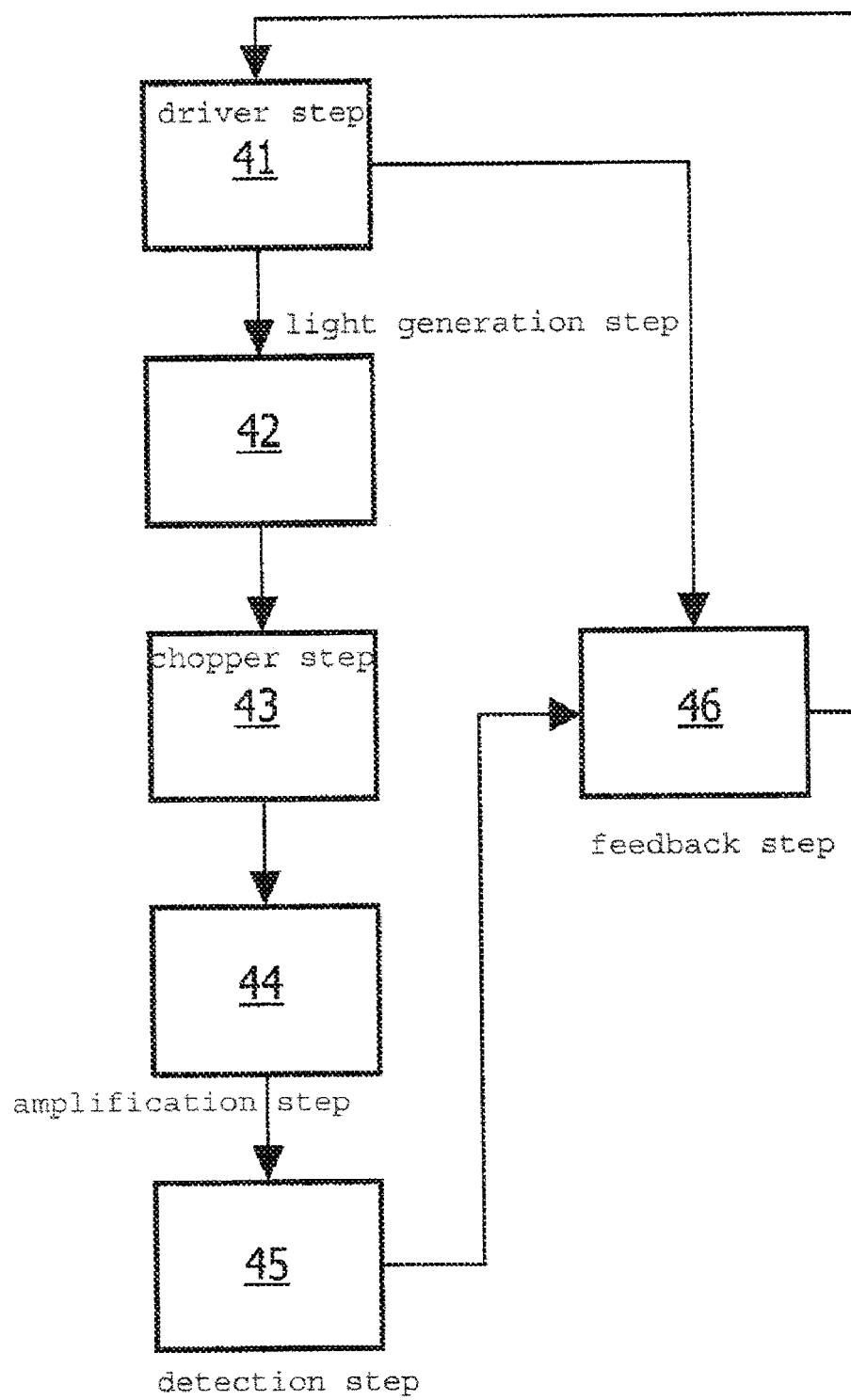
FIG. 4 shows a flow diagram of a feedback method for use with the invention.

FIG. 4 shows a flow diagram of a feedback method for use with the invention. In driver step 41 the light source driver sends a driving signal to the light source 101 and a reference signal to the feedback electronics 111. The driving signal and the reference signal comprise a small modulation at a modulation frequency $f_{mod}$. Then in light generation step 42, a continuous light beam is generated with a wavelength modulation corresponding to the modulation in the driving signal. In chopper step 43 light pulses are generated from the continuous light beam at a chopper frequency $f_{chop}$. In amplification step 44, if the length of the optical cavity matches the wavelength of the light, the light is amplified by the optical cavity. Thereafter, in detection step 45 a detector 110 measures the light intensity behind the optical cavity and provides a detector signal to the feedback electronics 111. In wavelength feedback step 46, the detector signal and the driving signal are processed to provide a feedback signal to the light source driver. Subsequently, the feedback signal is used by the light source driver to adapt the driving signal and the reference signal. With this feedback loop the average wavelength of the light beam is repetitively adapted to the cavity length. As elucidated above with reference to FIG. 3, the chopper frequency fchop is higher than the modulation frequency $f_{mod}$ to reduce the response time of the feedback loop.

Figure 5:
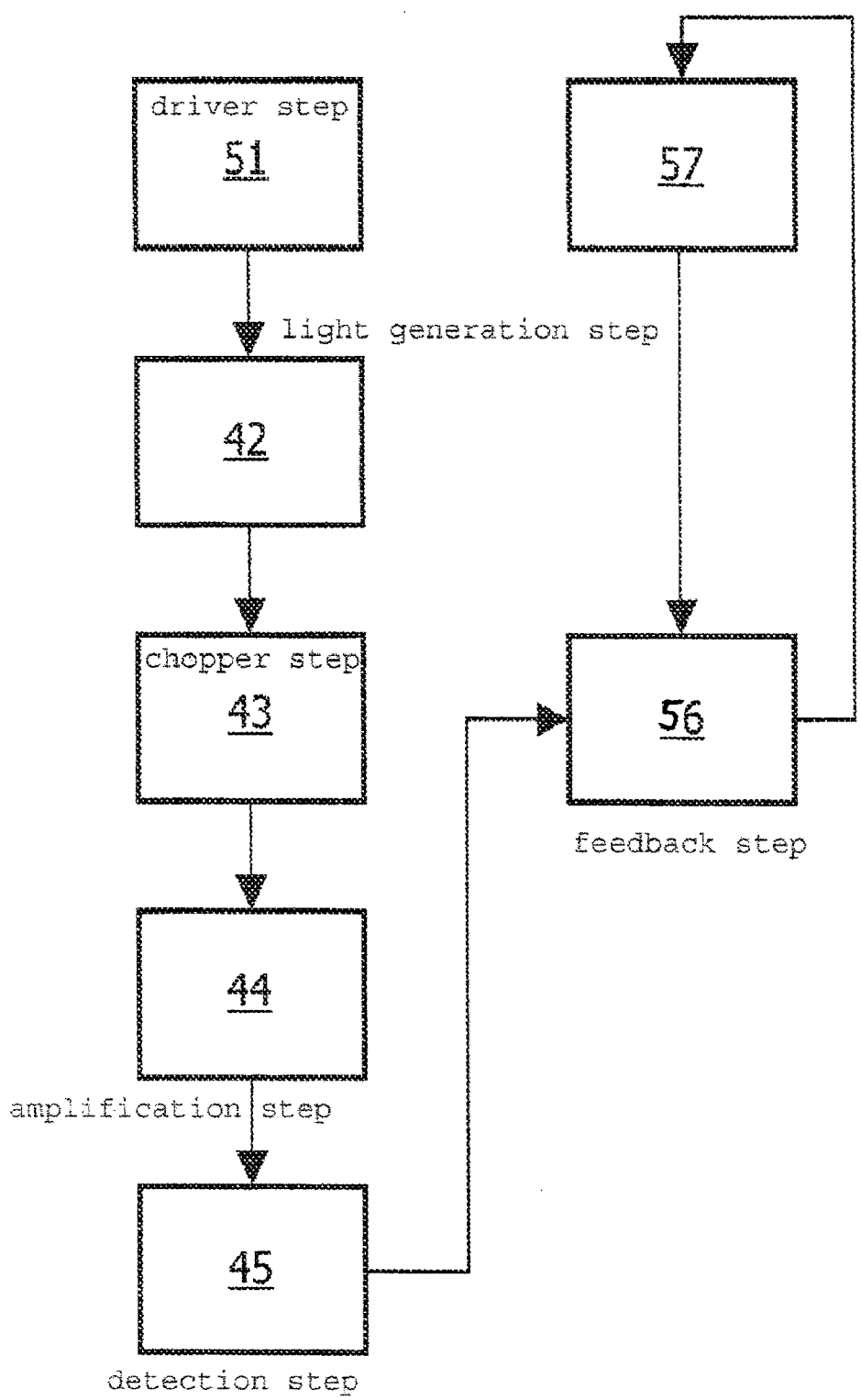

FIG. 5, shows a flow diagram of another feedback method for use with the invention. The method of FIG. 5 is similar to the method of FIG. 4. The main difference is that the wavelength of the light beam is not modulated. Instead, the length of the optical cavity is modulated. In step 51 the light source driver sends a driving signal to the light source 101. The driving signal is not modulated. In step 57, the mirror actuator 105, for example a piezo driver, modulates the position of at least one of the cavity mirrors 104a, 104b to change the length of the cavity. Simultaneously, a size reference signal, corresponding to the position modulation, is sent to the feedback electronics 111. The modulation of the position of the cavity mirror 104a, 104b is performed at the modulation frequency $f_{mod}$. The light generation step 42, chopper step 43, amplification step 44 and detection step 45 are performed just as describes with reference to FIG. 4. In size feedback step 56, the detector signal and the size reference signal are processed to provide a feedback signal to the mirror actuator 105. Subsequently, the feedback signal is used by the mirror actuator 105 to adapt the size of the optical cavity. With this feedback loop the cavity length is repetitively adapted to the average wavelength of the light beam. As elucidated above with reference to FIG. 3, the chopper frequency $f_{chop}$ is higher than the modulation frequency $f_{mod}$ to reduce the response time of the feedback loop.

It is to be noted that the advantageous combination of an optical cavity and a crystal oscillator could, in principal, also be achieved in trace gas detectors using different feedback loops and/or modulation schemes. When crystal oscillators are used instead of microphones it is important to use a chopping frequency that matches a resonance frequency of the crystal oscillator.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the claims enumerating several means, several of these means may be embodied by one and the same item of hardware. The mere fact that certain measures are recited in mutually different dependent claims does not indicate that a combination of these measures cannot be used to advantage.

What is claimed is:

1. A photo acoustic trace gas detector for detecting a concentration of a trace gas in a gas mixture, the photo acoustic trace gas detector comprising:
    a light source for producing a light beam;
    a light modulator for modulating the light beam into a series of light pulses at a chopping frequency for generating sound waves in the gas mixture, an amplitude of the sound waves being a measure of the concentration;
    an optical cavity for containing the gas mixture and for amplification of a light intensity of the light pulses;
    a transducer for converting the sound waves into electrical signals; and
    a feedback loop for regulating a ratio of a length of the optical cavity and a wavelength of the light beam for the amplification of the light intensity of the light pulses in the optical cavity, the feedback loop comprising:
        ratio modulating means for modulating the ratio at a modulation frequency;

a photo detector for measuring the light intensity of the light pulses; and adjusting means, coupled to the photo detector and to the ratio modulating means for, in dependence of the measured light intensity, adjusting an average of the ratio, wherein the chopping frequency is higher than the modulation frequency.

2. The photo acoustic trace gas detector according to claim 1, wherein the chopping frequency is at least three times higher than the modulation frequency.

3. The photo acoustic trace gas detector as claimed in claim 1, wherein the transducer is a crystal oscillator.

4. The photo acoustic trace gas detector as claimed in claim 3, wherein the crystal oscillator is a quartz tuning fork.

5. The photo acoustic trace gas detector according to claim 1, wherein the ratio modulating means are arranged for modulating the wavelength of the light beam.

6. The photo acoustic trace gas detector according to claim 1, wherein the ratio modulating means are arranged for modulating the length of the optical cavity.

* * * * *